United States Patent [19]

Orth et al.

[11] Patent Number: 4,661,115
[45] Date of Patent: Apr. 28, 1987

[54] HAIR DYEING AGENTS

[75] Inventors: Winfred Orth, Hassloch/Pfalz; Karl-Heinz Schrader, Bevern; Werner Fickert, Mannheim, all of Fed. Rep. of Germany

[73] Assignee: Ruetgerswerke Aktiengesellschaft, Frankfurt, Fed. Rep. of Germany

[21] Appl. No.: 826,646

[22] Filed: Feb. 6, 1986

[30] Foreign Application Priority Data

Mar. 8, 1985 [DE] Fed. Rep. of Germany ....... 3508265

[51] Int. Cl.$^4$ .............................................. A61K 7/13
[52] U.S. Cl. .......................................... 8/409; 8/423
[58] Field of Search ........................... 8/409, 423, 428

[56] References Cited

U.S. PATENT DOCUMENTS

| | | | |
|---|---|---|---|
| 3,536,436 | 10/1970 | Lange | 8/10.2 |
| 3,826,608 | 7/1974 | Wiskott | 8/10.1 |
| 3,862,157 | 1/1975 | Wiskott | 260/293.69 |
| 4,213,758 | 7/1980 | Rose et al. | 8/409 |
| 4,473,375 | 9/1984 | Claussen | 8/409 |
| 4,487,607 | 12/1984 | Rose et al. | 8/408 |
| 4,511,360 | 4/1985 | Monnais et al. | 8/405 |
| 4,567,272 | 1/1986 | Orth et al. | 546/281 |

FOREIGN PATENT DOCUMENTS 2714831 12/1978 Fed. Rep. of Germany .

Primary Examiner—A. Lionel Clingman
Assistant Examiner—Brooks Alan Truskett
Attorney, Agent, or Firm—Beveridge, DeGrandi & Weilacher

[57] ABSTRACT

New coupling or shading (nuance) components are described which in combination with pertinent developers are used for dyeing of hair. These coupling components are dinitropyridine derivatives of the general formula:

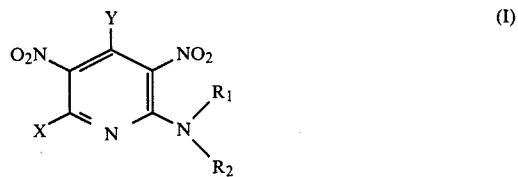

(I)

whereby the substituents X, Y, $R_1$ and $R_2$ have the meaning given.

8 Claims, No Drawings

HAIR DYEING AGENTS

The invention relates to hair dyeing agents on the basis of oxidation dyestuffs in combination with pertinent developers. The coloration of the hair takes place thereby as a result of reaction of the developer substances with so-called coupler substances or shading (nuance) agents in an alkaline medium in the presence of a suitable oxidation agent. As a result of the intensive colors that are generally obtained thereby with good characteristics of genuineness and as a result of the great extent of the range in variation of color tones, these oxidation dyes play an important role in hair cosmetics.

As coupler or shading components, m-phenylene diamine derivatives, phenols, naphthols or resorcin derivatives have been known. Since all of these products are not generally regarded as safe toxicologically and dermatologically, attempts were made to shift over to the pyridine amino compounds which are considered to be safer.

Thus, there has been described the use as a coupling substance of 2,3- or 2,6-diaminopyridine from the West German Pat. No. 11 42 045; 2,5-diaminopyridine from East German Pat. No. 57 402; bis-aminopyridines from European Pat. No. 0008079 B 1; dihydroxypyridines from U.S. Pat. No. 1,571,570; hydroxy- and alkoxypyridine amines from French Pat. Nos. 1,397,551 and 1,398,193 and pyridylaminobenzenes and bispyridylamines from French Pat. No. 1,401,469.

Aminopyridine compounds, however, are oxidation sensitive with respect to the oxygen in the air. In order to compensate for losses which occur even during the storing of the preparation as well as during use thereof, these compounds are utilized in larger quantites than would be necessary per se for the coloring process. In addition, these amino compounds are used as salts in order thus to achieve a stabilization during storage. As a result of that, however, other disadvantages arise: Because of the higher number of ions present which is necessitated by the formation of the corresponding salt, the brilliance of the color tones is decreased. Moreover, these salts in higher concentrations, may not be combined with all surface active agents so that not all desirable galenic forms of the hair dyeing agents may be produced.

Therefore, the object of the invention pertains to the development of hair dyeing agents on the basis of oxidation dyestuffs which result in intensive colors with very good characteristics of genuineness in a wide range of variation in color tones and the coupling nuance components of which are safe toxicologically and dermatologically and essentially stable with regard to the oxygen of the air, so that they may also be used in lesser quantity in neutral or salt form.

The object of the invention is achieved by a composition for the dyeing of hair, such as human hair, on the basis of an oxidation dyestuff system which contains pertinent developer components used in such systems, and further, wherein there is present a dinitropyridine derivative of the general formula (I), or mixture of such derivatives:

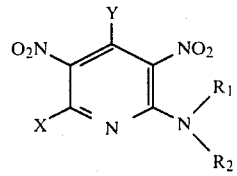

wherein $R_1$ and $R_2$ are the same or different and represent hydrogen, an alkyl group with 1–4 C atoms, an unsubstituted phenyl group, a phenyl group substituted at any position with one or more amino-, methylamino-, dimethylamino-, hydroxy-, alkyl- or alkoxy group with 1–2 C atoms, a cycloalkyl group with 1 to 7 C atoms or an unsubstituted or methyl-, ethyl- or propyl substituted pyrrolo, pyridino-, piperidino-, pyrimidino-, piperazino- or morpholino group or an alkenyl group of the general formula (II):

$$-R-Z \qquad (II)$$

wherein R represents an alkyl chain of 1–6 C atoms or a phenyl group and Z is an hydroxy- and/or an alkoxy group with 1–3 C atoms that may be substituted at any position position, or an amino group of the general formula (III):

in which $R_3$ and $R_4$ are the same or different and represent hydrogen, an unsubstituted or hydroxy- or amine substituted alkyl-, aralkyl-, cycloalkyl group at any position with up to 7 C atoms, an unsubstituted phenyl or phenyl substituted at any position with one or more amino-, methylamino-, dimethylamino-, hydroxy-, alkyl- or alkoxy groups with 1–2 C atoms, or an unsubstituted or pyrrolo-, pyridino-, piperidino-, pyrimidino-, piperzino- or morpholino group substituted at any given position with methyl-, ethyl-, or propyl, and X represents either hydrogen, an hydroxy- or aminoalkyl- or alkoxy group with 1–4 C atoms or an amino group of the general formula (I)

and Y is hydrogen, an alkyl group with 1–3 C atoms or an unsubstituted or hydroxy- or amino substituted phenyl group.

It has been determined that dinitropyridine derivatives of the general formula (I):

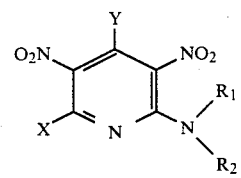

in combination with pertinent developer components and oxidation agents represent ideal coupling nuance components which fulfill the requirements mentioned above. Any suitable conventional hair dyeing oxidation agent and developer therefor may be used for purposes of the present invention. Those terms are well understood in the art.

It has been generally known that the nitro group raises the oxidation resistance of pyridine derivatives. Up to this point in time this knowledge has also prevented the use of nitropyridine derivatives in hair dyeing agents on the basis of oxidation dyestuffs, because the products used in those systems must react easily with a conventional oxidation agent. Therefore, certain nitropyridine derivatives, such as those from German Pat. No. 19 49 750 are known as self-developing hair dyes, but are not known for use in dyeing agents on the basis of oxidation colors. Surprisingly, even the dinitropyridine derivatives according to the invention are sufficiently stable against oxygen in the air so that they may also be used in their non-ionic form. However, they are nevertheless so reactive that they will react with conventional oxidation agents in a manner known per se in the sense of the coloration.

It has been furthermore found that the dinitropyridine derivatives according to the invention may be considered as safe toxicologically as well as dermatologically. This is surprising insofar as it has been known from the chemistry of aromatic substances that the nitro products generally show a higher toxicity than the non-nitrated aromatic substances.

Further advantages of the hair dyeing compositions according to the invention are extremely brilliant color tones which in the case of use of the known aminopyridine coupler substances may not be achieved, as well as a stronger coloration despite low quantities used. This last effect is partially conditional on the color giving effect of the nitro groups and partially conditional on the oxidation stability. As a result of that, with approximately half the quantities of the dinitropyridine derivatives according to the invention instead of the hitherto used aminopyridine derivatives it is possible to achieve equally deep but more brilliant color tones.

As a result of the variation of the substituents on the pyridine ring and on the amino group of the dinitropyridine compounds used according to the invention, many color variations may be achieved. It is thus possible with these means by mixing various shading components to adjust many color variations with an oxidation color system. The hair dyeing agents according to the invention thus represent an enrichment in the field of hair cosmetics.

Coupling and nuance shading components to be used in oxidation dye systems according to the invention are theoretically all pyridine derivatives which each contain a nitro group in the 3- and 5- position and at least a substituted or unsubstituted amino group in the 2-position in the pyridine ring, where the position 6 is either unsubstituted or substituted by an alkoxy-, hydroxyalkyl-, or aminoalkyl- group or a substituted or unsubstituted amino group, and the position 4 is either unsubstituted or substituted by a short chain alkyl- or an unsubstituted or substituted phenyl group. Products which are suitable for commercial purposes should be soluble in water, possibly as a salt or in mixture with a solvent therefor and should be stable, so that as a result certain limitations apply concerning the substituents as will be apparent to those skilled in the art. In practice therefore, the dinitropyridine derivatives are preferred which correspond to the general formula (I):

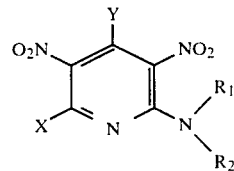

(I)

The substituents have the following meaning: X is hydrogen, an aminoalkyl-, hydroxyalkyl-, or alkoxy group with 1-4 C atoms or an amino group. Examples of such substituents are the following groups: aminomethyl-, aminoethyl-, aminopropyl-, amino-i-propyl-, aminobutyl-, hydroxymethyl-, hydroxyethyl-, hydroxypropyl-, hydroxybutyl-, methoxy-, ethoxy-, or propoxy-.

The amino group corresponds as the amino group in the 2-position to the general formula:

These amino groups in the 2- and 6- position can be the same or different. Y is hydrogen, a methyl-, ethyl-, propyl-, i-propyl-, phenyl-, hydroxyphenyl- or an aminophenyl group.

The substituent —NR$_1$R$_2$ can be unsubstituted or substituted amino group, wherein R$_1$ and R$_2$ are the same or different and represent hydrogen, an alkyl group with 1-4 C atoms, an unsubstituted or substituted phenyl having at one or more positions an amino-, methylamino-, dimethylamino-, hydroxy-, alkyl- or alkoxy group with 1-2 C atoms, a cycloalkyl group with 1 to 7 C atoms or an unsubstituted or substituted heterocyclic group with a methyl-, ethyl-, or propyl group.

Examples of these amino groups are methyl-, ethyl-, propyl-, i-propyl-, butyl-, i-butyl-, tert-butyl-, dimethyl-, diethyl-, methyl-ethyl-, dipropyl-, di-i- propyl-, methyl-propyl-, cyclohexyl-, phenyl-, aminophenyl-, diaminophenyl-, methylaminophenyl-, dimethylaminophenyl-, hydroxyphenyl-, dihydroxyphenyl-, tolyl-, xylyl-, ethylphenyl-, methoxyphenyl-, ethoxyphenyl- or dimethoxyphenylamino groups as well as pyrrolo-, methylpyrrolo-, ethylpyrrolo-, propylpyrrolo-, pyridino-, methylpyridino-, ethylpyridino-, dimethylpyridino-, propylpyridino-, piperidino-, methylpiperidino-, ethylpiperidino-, propylpiperidino-, pyrimidino-, methylpyrimidino-, ethylpyrimidino-, propylpyrimidino-, piperazino-, methylpiperzino-, ethylpiperazino-, propylpiperazino-, morpholino-, methylmorpholino-, ethylmorpholino-, or propylmorpholino groups.

The substituents R$_1$ and R$_2$ however may also represent an alkenyl group of the general formula:

—R—Z whereby R signifies an alkyl chain with 1-6 C atoms or a phenyl group and Z signifies an hydroxy- and/or alkoxy group with 1-3 C atoms, substituted at any given position, or an amino group of the general formula:

wherein $R_3$ and $R_4$ are the same or different and represent hydrogen, or alkyl-, aralkyl-, cycloalkyl groups with 1 to 7 C atoms or such groups substituted by hydroxy- or amino, an unsubstituted phenyl or phenyl substituted at any position with one or more amino-, methylamino-, dimethylamino-, hydroxy-, alkyl- or alkoxy groups of 1–2 C atoms, or an unsubstituted pyrrolo-, pyridino-, piperidino-, pyrimidino-, piperazino- or morpholino, or such group substituted at any position by methyl- ethyl- or propyl-.

Examples of such amino groups are hydroxymethyl-, hydroxyethyl-, hydroxypropyl-, hydroxyisopropyl-, hydroxybutyl-, hydroxypentyl-, hydroxyhexyl-, methoxymethyl-, ethoxymethyl-, propoxymethyl-, isopropoxymethyl-, hydroxymethoxymethyl-, hydroxyethoxymethyl-, methoxyethyl-, ethoxyethyl-, aminomethyl-, aminoethyl-, aminopropyl-, aminobutyl-, aminopentyl-, aminohexyl-, aminocyclohexyl-, methylaminomethyl-, methylaminoethyl-, methylaminopropyl-, dimethylaminomethyl-, dimethylaminoethyl-, dimethylaminopropyl-, ethylaminomethyl-, propylaminomethyl-, diethylaminomethyl-, ethylaminoethyl-, diethylaminoethyl-, ethylaminopropyl-, diethylaminopropyl-, bis-aminomethyl-, bis-aminoethyl-, bis-aminopropyl-, bis-aminobutyl-, bis-aminopentyl-, bis-aminohexyl-, hydroxyphenyl-, methoxyphenyl-, tolyl-, dimethoxyphenyl-, aminophenyl-, phenyl-, diaminophenyl-, pyrrolmethyl-, pyrrolethyl-, methylpyrrolmethyl-, methylpyrrolethyl-, pyridinmethyl-, pyridinethyl-, pyridinpropyl, methylpyridinmethyl-, methylpyridinethyl-, dimethylpyridinmethyl-, dimethylpyridinethyl-, ethylpyridinmethyl-, ethylpyridinethyl-, piperidinmethyl-, piperidinethyl-, methylpiperidinmethyl-, ethylpiperidinethyl-, piperazinmethyl-, piperazinethyl-, methylpiperazinmethyl-, methylpiperazinethyl-, ethylpiperazinmethyl-, ethylpiperazinethyl-, pyrimidinmethyl-, pyrimidinethyl-, pyrimidinpropyl-, methylpyrimidinmethyl-, morpholinmethyl-, methylmorpholinmethyl-, ethylmorpholinmethyl-, morpholinethyl-, methylmorpholinethyl-, ethylmorpholinethyl-, propylpyrrolmethyl-, propylpyridinmethyl-, propylpiperinmethyl-, propylpyrimidinmethyl-, propylpiperazinmethyl- or proplymorpholinmethylamino-.

The nuance components according to the invention may be used either by themselves or for the adjustment of the desired color shadings and nuances in mixtures with one another or with other shading or coupler components known in the art.

As examples of developer components that are suitable for use in the hair dyeing compositions of the present invention there are primary aromatic amines with a functional group in the p-position such as
p-phenylenediamine, alkylamino-p-phenylenediamine
p-toluylenediamine,
p-aminophenol,
N-methyl-p-phenylenediamine,
N,N-dimethyl-p-phenylenediamine,
N,N-diethyl-2-methyl-p-phenylenediamine,
N-ethyl-N-hydroxyethyl-p-phenylenediamine,
Chloro-p-phenylenediamine,
N,N-bis-hydroxyethylamino-p-phenylenediamine,
methoxy-p-phenylenediamine,
2,6-dichloro-p-phenylenediamine,
2-chloro-6-bromo-p-phenylenediamine,
2-chloro-6-methyl-p-phenylenediamine,
6-methoxy-3-methyl-p-phenylenediamine.

Other compounds of this technology may also be used, which contain one or more functional groups such as OH-group, $NH_2$-groups, NHR-groups, $NR_2$-groups, wherein R represents an alkyl- or hydroxyalkyl group with 1–4 C atoms such as heterocyclic hydrazone derivatives such as 1-methylpyrrolidono-(2)-hydrazone,
4-aminopyrazonlone derivatives such as 4-amino-1-phenyl-3-carbamoylpyrazolon-5, N-butyl-N-sulfobutyl-p-phenylenediamine,
Tetraaminopyrimidines such as:
2,4,5,6-tetraaminopyrimidine,
4,5-diamino-2,6-bismethylaminopyrimidine,
2,5-diamino-4-diethylamino-6-methylaminopyrimidine,
2,4,5-triamino-6-dimethylaminopyrimdine,
2,4,5-triamino-6-piperidino-pyrimidine,
2,4,5-triamino-6-anilino-pyrimidine,
2,4,5-triamino-6-morpholinopyrimidine,
2,4,5-triamino-6-$\beta$-hydroxy-ethylaminopyrimidine
and also pyridine derivatives such as, for example, 2,5-diaminopyridine or 2,5-diamino-4-methylpyridine.

The oxidative coupling, that is the development of the coloration could basically take place also through the oxygen in the air just as in the case of other oxidation hair dye substances. However, for practical use, the reaction speed is too low and the color development on the hair too slow. Therefore, it is preferable to use chemical oxidation agents. As such, particularly hydrogen peroxide or its addition products with urea, melamine and sodium borate as well as mixture of such hydrogen peroxide addition compounds with potassium peroxide disulfide can be used.

The hair dyeing agents according to the invention which contain the shading (nuance) and developer components can be prepared for use in corresponding cosmetic preparations such as creams, elusions, gels or also simply solutions. For that purpose, it is sometimes necessary to heat the solutions up to 100° C. in order to place the components into solution, if necessary with the help of a dissolving agent. At the same time, the concentrations of nuance components in the products that may be used ranges from 0.01 to 2% by weight and that of the developer components ranges from 0.1 to 5% by weight. For the production of the cosmetic preparations, the components are mixed with the additional components customary for such preparations. As such additional components one may enumerate for example ammonium hydroxide, linking or emulsifying agents of the anionic or non-ionic type, such as alkyl benzol sulfonates, fatty alcohol sulfonates, fatty alcohol ether sulfates, amine oxide, alkyl sulfonate, fatty acid alkanol amide, alkylphenol oxalkylate and addition products of ethylene sulfite, sodium dithionite, thiogycol acid or ascorbic acid, thinning agents such as methyl cellulose, higher fatty alcohols, fatty acids, furthermore perfume oils and hair conditioners such as pantothenic acid and chloesterol. Such conventional additives are well known in the art and may be used to obtain the desired expected result.

Shortly before using these compositions, the hair dyeing agents are mixed with the solution of one of the cited oxidation agents as is customary and the mixture obtained thereby is applied to the hair. The application temperatures at the same time should be in the range of 30° to 40° C. After a reaction time of about 30 minutes, the hair dyeing agent is removed from the hair that is to be dyed by rinsing. Afterwards, the hair is rewashed with a mild shampoo and is dried. Rinsing and washing of the hair are carried out in the conventional manner.

The following examples serve to illustrate the present invention but are not limiting thereof.

In the examples of hair dyeing agent of the following basic composition was used and dyeing experiments carried out:

2% by weight of 30% fatty acid aminoxide (dimethyldodecylaminoxide) solution;
0.5% by weight of sodium dithionite;
10% by weight of 25% ammonium hydroxide;
0.5% by weight of nuance component according to the invention;
1% by weight of p-toluylene diamine sulfate; and
86% by weight of water.

100 ml of the hair dyeing agent are mixed with 10 ml of hydrogen peroxide (6%). Into this mixture, strands of human hair are dipped and the color solution is allowed to act on it for 30 minutes at 35° C. Subsequently, the strands are rinsed well with water, are dried and are evaluated with regard to their coloration.

Shading components used according to the invention:

EXAMPLE 1

2-amino-6-methoxy-3,5-dinitropyridine

Color effect: brown coloration with a slight tint of green

EXAMPLE 2 b 2-dimethylamino-3,5-dinitropyridine

Color effect: bluish black

EXAMPLE 3

2,6-bis-(2-hydroxyethylamine)-3,5-dinitropyridine

Color effect: hazelnut type brown coloration

EXAMPLE 4

6-methoxy-3,5-dinitro-2-propylaminopyridine

Color effect: hazelnut type brown coloration

EXAMPLE 5

2,6-bis (N,N-dimethylamino)-3,5-dinitropyridine

Color effect: middle blond

In commercial practice, the oxidation hair dyeing compositions may be packaged and sold in a variety of ways. For example, the oxidation hair dyes can be sold in a two component kit containing the coupling nuance agent mixed together with the developer in one package and the oxidizing agent in a second package. The customer purchasing the kit will receive both packages and will then open both packages and mix the contents together according to instructions prior to application to the hair.

In another embodiment, the oxidation hair dyes can be sold in a kit containing three separate component packages; i.e. one package containing the coupling nuance agent together with water and other conventional additives such as finely divided silicas in a paste or gel; a second package containing the developer together with conventional additives such as surface active agents, sodium dithionite, ammonium hydroxide and the like, and a third package containing the oxidizing agent and any conventional additives, water, silica, etc. The three packages are then opened and mixed by the user when ready to dye the hair.

The exact formulations, additives and packaging selected are matters within the scope of a person skilled in this art based on the foregoing description.

Further variations and modifications of the invention will become apparent from the foregoing and are intended to be encompassed by the claims appended hereto.

The German priority application No. P 35 08 265.8 is relied on and incorporated herein.

We claim:

1. A composition for the dyeing of hair comprising at least one oxidation dyestuff, at least one developer for said oxidation dyestuff and as the coupling agent a sufficient amount of a dinitropyridine derivative of the formula (I) or mixture of said derivatives:

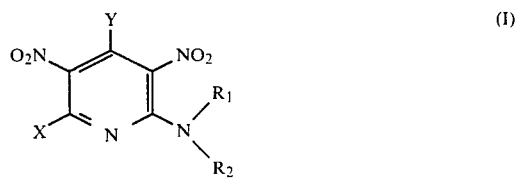

wherein $R_1$ and $R_2$ are the same or different and represent hydrogen, alkyl with 1–4 C atoms, an unsubstituted phenyl, phenyl substituted at any position by one or more amino-, methylamino-, dimethylamino-, hydroxy-, alkyl- or alkoxy group with 1–2 C atoms, cycloalkyl with 1 to 7 C atoms or an unsubstituted pyrrolo, pyridino, piperidino, pyrimidino, piperazino or morpholino, or methyl-, ethyl- or propyl substituted pyrrolo-, pyridino-, piperidino-, pyrimidino-, piperazino- or morpholino or alkenyl of the formula (II):

wherein R represents alkyl of 1–6 C atoms or phenyl and

Z is hydroxy- and/or alkoxy with 1–3 C atoms, or an amino group of the formula (III):

in which $R_3$ and $R_4$ are the same or different and represent hydrogen, unsubstituted or hydroxy- or amine substituted alkyl-, aralkyl-, cycloalkyl with 1 to 7 C atoms; an unsubstituted phenyl or phenyl substituted at any position with one or more amino-, methylamino-, dimethylamino-, hydroxy-, alkyl-, or alkoxy group with 1–2 C atoms; or any methyl-, ethyl-, or propyl substituted or unsubstituted pyrrolo-, pyridino-, piperidino-, pyrimidino-, piperazino- or morpholino-;

X represents hydrogen, an hydroxy- or aminoalkyl- or alkoxy group with 1–4 C atoms or an amino group of the formula (I)

and Y is hydrogen, an alkyl group with 1–3 C atoms or an unsubstituted phenyl or hydroxy- or amino substituted phenyl.

2. The composition according to claim 1 wherein the dinitropyridine compound is 2-amino-6-methoxy-3,5-dinitropyridine.

3. The composition according to claim 1 wherein the dinitropyridine compound is 2-dimethylamino-3,5-dinitropyridine.

4. The composition according to claim 1 wherein the dinitropyridine compound is 2,6-bis-(2-hydroxyethylamine)-3,5-dinitropyridine.

5. The composition according to claim 1 wherein the dinitropyridine compound is 6-methoxy-3,5-dinitro-2-propylaminopyridine.

6. The composition according to claim 1 wherein the dinitropyridine compound is 2,6-bis (N,N-dimethylamino)-3,5-dinitropyridine.

7. A hair dyeing formulation kit including a first component comprising a coupling nuance agent in a sufficient derivative, or mixture, of the formula (I) as defined herein, and a developer;

and a second component comprising an oxidizing agent in a sufficient amount, said first and second components being unmixed in said kit.

8. A hair dyeing formulation kit including a first component comprising a coupling nuance agent in a sufficient amount which is a nitropyridine derivative, or mixture, of the formula (I) as defined herein;

a second component comprising a developer for said hair dyeing; and a third component comprising an oxidizing agent in a sufficient amount, said components being unmixed in said kit.

* * * * *